United States Patent [19]

Naslund et al.

[11] 4,256,590

[45] Mar. 17, 1981

[54] MODIFIED HETEROPOLYSACCHARIDES AND THEIR PREPARATION

[75] Inventors: Lars A. Naslund, Morganville, N.J.; Allen I. Laskin, New York, N.Y.

[73] Assignee: Exxon Research & Engineering Co., Florham Park, N.J.

[21] Appl. No.: 28,967

[22] Filed: Apr. 11, 1979

Related U.S. Application Data

[60] Division of Ser. No. 794,725, May 9, 1977, Pat. No. 4,182,860, which is a continuation-in-part of Ser. No. 630,468, Nov. 10, 1975, abandoned.

[51] Int. Cl.$^3$ .................... E21B 43/22; C12P 19/06
[52] U.S. Cl. ............................. 252/8.55 D; 166/246
[58] Field of Search ................ 252/8.55 D; 536/114; 435/104; 166/246

[56] References Cited

U.S. PATENT DOCUMENTS

| 2,773,752 | 11/1973 | Buchanan et al. ............... 536/114 |
| 3,801,502 | 4/1974 | Hitzman ...................... 252/8.55 D |
| 4,135,979 | 1/1979 | Corley et al. ................. 536/114 X |

OTHER PUBLICATIONS

Patton, SPE Paper 4670, Delivered at 48th Annual Fall Meeting of Society of Petroleum Engineers of AIME, Las Vegas, Nevada, Sep. 30–Oct. 3, 1973.

Lipton, SPE paper 5099, Delivered at 49th Annual Fall Meeting of Society of Petroleum Engineers of AIME, Houston, Texas, Oct. 6–9, 1974.

Jeanes et al., *J. Applied Polymer Science,* vol. V, No. 17, 1961, pp. 519–526.

Jeanes et al., *J Applied Polymer Science,* vol. 8, 1964, pp. 2775–2787.

*Primary Examiner*—Herbert B. Guynn
*Attorney, Agent, or Firm*—Albert P. Halluin; James H. Takemoto

[57] ABSTRACT

A composition containing a heteropolysaccharide produced by the action of bacteria of the genus Xanthomonas, wherein the heteropolysaccharide has been modified by heating, at a temperature of at least 100° C. for 1 to about 300 minutes, an aqueous solution containing native, untreated heteropolysaccharide produced by the action of bacteria of the genus Xanthomonas, and at least about 0.5 weight percent salt. The solution is preferably filtered or otherwise treated to separate the modified heteropolysaccharide from bacterial cells, cellular debris and other materials, prior to being put to use in, e.g., oil recovery processes, additive for foodstuffs, pharmaceutical preparations, etc.

6 Claims, No Drawings

MODIFIED HETEROPOLYSACCHARIDES AND THEIR PREPARATION

CROSS REFERENCE TO RELATED APPLICATIONS

This application is a division of application Ser. No. 794,725, filed May 9, 1977, now U.S. Pat. No. 4,182,860, which is a continuation-in-part of application Ser. No. 630,468, filed Nov. 10, 1975, now abandoned.

BACKGROUND OF THE INVENTION

1. Field of the Invention

The present invention relates to heteropolysaccharides produced by bacteria of the genus Xanthomonas and to methods for modifying such heteropolysaccharides. The invention further relates to an improved method for recovering oil from a subterranean oil-bearing formation.

2. Description of the Prior Art

Heteropolysaccharides produced by the action of bacteria of the genus Xanthomonas are used in many applications. They are used in many foodstuffs and beverages. They are used as suspending agents in many cosmetic and pharmaceutical preparations. For these uses a biopolymer which will form solutions of high clarity or which will not undesirably discolor the preparations is needed. Biopolymers are also used as a viscosifier for water which is injected into oil-bearing subterranean formations. This viscous water will more readily displace oil from the formation in most instances than will water which does not contain the polymer. Because of the need for a readily injectable biopolymer for oil recovery purposes, the remainder of this discussion of the prior art will be directed to general problems of recovering oil from subterranean formations, of using materials to increase the viscosity of water used to displace oil from such reservoirs, and of producing a viscosifier which can be more readily injected into such formations.

Recognition that techniques utilized in the initial exploitation of subterranean oil-bearing reservoirs generally permit the recovery of only a small fraction of the total oil originally present in such reservoirs has led to the development of a number of secondary and tertiary (enhanced) recovery processes designed to stimulate production after the natural energy of the reservoir has been largely expended. The most widely used of these is the waterflooding process. By simply injecting water into an underground reservoir through one or more injection wells under sufficient pressure to force it in the direction of production wells spaced some distance from the injection wells, much of the oil left in the reservoir after the wells have ceased to flow at an economical rate can be recovered. The waterflooding process is considerably more attractive than many other enhanced recovery processes of the displacement type because the water utilized can ordinarily be obtained at little cost and need not be recovered from the reservoir in order to make the process economically feasible.

Despite the obvious advantages of waterflooding as an enhanced recovery technique, it has often suffered by comparison with other processes. Field evaluations have shown that waterflooding permits the recovery of much oil that cannot be produced by primary recovery techniques but that considerable quantities of oil nevertheless remain in the reservoir following a waterflooding operation. The principal reason for this appears to be the tendency of the injected water to finger through the sections of the reservoir offering the least resistance and to thus bypass much of the oil present in the reservoir. In addition, it has been demonstrated that capillary and surface forces prevent the displacement of appreciable quantities of the oil present in those sections of the reservoir through which the water actually passes.

Fundamental investigations into the mechanisms by which one fluid displaces another within a porous medium have demonstrated that the relative viscosities of the two fluids play an important role in determining the efficiency of the displacement. It can be shown that the displacement efficiency is directly related to the ratio of viscosity of the displacing fluid to that of the displaced fluid. Petroleum normally ranges in viscosity from one to two centipoises up to about 1,000 centipoises or more, depending upon the particular oil reservoir in which it is found. The viscosity of water, on the other hand, is less than one centipoise under the conditions prevailing in most subterranean oil-bearing reservoirs. The ratio of the viscosity of water to that of oil is therefore low, and hence high displacement efficiencies during enhanced recovery processes using water as the displacing agent are not to be expected.

In view of this effect of the viscosity ratio upon displacement efficiency, it has been suggested that a more viscous liquid than water be employed as a displacing agent during enhanced recovery operations. Economic considerations dictate that the liquid so used be an aqueous solution. A variety of polymeric materials and other thickening agents have been advocated as useful for preparing such solutions. Tests have demonstrated that many of the materials proposed heretofore are not usable, even though they can be employed to form relatively viscous aqueous solutions, because they lack other properties essential to a satisfactory thickener for enhanced recovery purposes. Some of the materials proposed in the past are relatively expensive and must be used in concentrations which make the cost prohibitive. Moreover, solutions of many such materials tend to plug the pore spaces of the permeable rock which makes up most oil reservoirs and hence would be unsatisfactory even if their use were economically feasible. Other materials are decomposed, seriously degraded, or precipitated at the temperature prevailing in many sub-surface reservoirs and by contact with reservoir sands and connate waters. Still other materials are adsorbed onto the rock surfaces within the reservoirs to such an extent that any increase in viscosity attained is lost almost immediately following injection of solutions of the materials into an injection well.

Considerable interest in microbially produced polysaccharides has been exhibited in recent years. Impetus has been given to the development of this interest by the discovery that certain polysaccharides formed by biochemical synthesis have properties which permit their use as thickening agents for water used in enhanced recovery operations carried out in the petroleum industry. It has been found that some of these materials added to water or brine in suitable concentrations produce viscous solutions which are relatively stable under the conditions which prevail in sub-surface oil reservoirs. By utilizing a solution of controlled viscosity in place of the water or brine normally employed in waterflooding projects, a more favorable mobility ratio can be obtained between the oil in the reservoir and the liquid used to displace it. The tendency of the displacing medium to finger through highly permeable sections of the reservoir without displacing oil from the less permeable sections is greatly decreased. Viscous forces which normally reduce the displacement efficiency in portions of the reservoir through which the displacing medium actually passes are more readily overcome. As a result of these effects, the use of water or brine containing polysaccharide thickening agents generally permits the recovery of significantly greater quantities of oil during waterflooding than can be recovered with water or brine alone.

In U.S. Pat. No. 3,305,016 to Lindblom et al there is disclosed a particularly effective polysaccharide for use as a thickening agent during oil field waterflooding operations, i.e., the heteropolysaccharide produced by the action of bacteria of the genus Xanthomonas upon sugar, starches, other carbohydrates, methanol, ethanol, and acetates. Studies and comparative tests have shown that this material, a polymer generally containing mannose, glucose, glucuronic acid and pyruvic acid, has much greater thickening power than dextran and similar polysaccharides and hence can be used in significantly lower concentrations than the other materials. It is effective in both fresh water and brine and has excellent high temperature stability. It is not precipitated or adsorbed to a significant extent upon contact with porous rock and sands commonly found in oil-bearing reservoirs. The combination of all of these properties makes the heteropolysaccharide formed by Xanthomonas considerably more attractive than other polysaccharides for use as water thickeners in enhanced recovery operations.

One difficulty that has been experienced with the use of Xanthomonas heteropolysaccharides as viscosifiers in flood waters is their tendency to plug the formations into which they are injected. This plugging problem is especially serious in oil reservoirs where salt concentrations in the water are high. These tendencies are generally thought to result from one or more of several factors; e.g. precipitation which occurs when solutions containing multivalent cations are injected into the formations containing alkaline materials; clumps of incompletely solubilized polymer; residual proteinaceous materials and/or residual whole bacterial cells or other cell debris from the fermentation process which produces the heteropolysaccharide.

A number of suggestions have been advanced to overcome the limitations with respect to the injectivity and/or the stability and clarity of these biopolymer solutions. For example, U.S. Pat. No. 3,355,447 to O'Connell, suggests heating an aqueous solution of the heteropolysaccharide under slightly alkaline conditions to moderate temperatures ranging up to 80° C. for a period of time. This solution is subsequently cooled and filtered. This technique is essentially a pasteurization process which does show some benefit in decreasing the spoilage of heteropolysaccharide solutions over a period of time. However, the resulting solution does not have significantly improved injectivity characteristics.

U.S. Pat. No. 3,591,578 to Colin and Guihert, discloses another technique for improving the viscosity of aqueous solutions of heteropolysaccharide, especially solutions in hydrochloric acid medium and also solutions in various acid- or salt-containing media. In this technique, the broth is heated subsequent to fermentation to a temperature in the range of 80° C. to 130° C. for a period of 10 to 120 minutes at a pH of 6.3 to 6.9. The patent does not disclose that the heat-treated heteropolysaccharides have injectivity properties as hereinafter described and claimed.

A proposal for clarifying heteropolysaccharide solutions is disclosed in U.S. Pat. No. 3,711,462 to Abdo. In this technique bacterial debris is removed from aqueous solutions of the heteropolysaccharide material by contacting the solution with a montmorillonite clay to adsorb the debris. Mono- or divalent salts are added, if not already present in this solution, and a clay coagulant is mixed with this solution to flocculate the clay and adsorb debris which is ultimately removed from the clarified solution by mechanical means. This patented technique does improve the clarity of the heteropolysaccharide solution; however, injectivity is not significantly improved.

An approach to the problems of clarity and flowability is disclosed in U.S. Pat. No. 3,729,460 to Patton. In this technique the heteropolysaccharide is treated at elevated temperatures (up to 120° C.) and under alkaline conditions, preferably, in a pH range from 11.2 to 12.8. It is disclosed that the technique improves the clarity and flowability of the heteropolysaccharide solution. However, it has been reported by Lipton that this patented technique does not completely solve the injectivity problem and the technique is reported to show very poor reproducibility (Lipton, "Improved Injectability of Biopolymer Solutions," SPE paper 5099, delivered at the 49th Annual Fall Meeting of the Society of Petroleum Engineers of AIME, Houston, Texax, October 6–9, 1974).

A more recent development is disclosed in U.S. Pat. No. 3,801,502 to Hitzman where heteropolysaccharides useful as waterflood viscosifiers are prepared by adding 0.05 to 5 wt. % of at least one additive selected from the group consisting of alcohols, phenols, ketones and nonionic surfactants to the fermentation effluent containing the heteropolysaccharide followed by heating the same to increase the viscosity of the solution or dispersion containing the heteropolysaccharide to a desired level. Patentee states that the heteropolysaccharide can be dissolved or dispersed in water or brine and thereafter the resulting solution or dispersion is heated with an alcohol, ketone, phenol or nonionic surfactant. This patent, however, does not teach or suggest that a heteropolysaccharide having improved injectivity properties as herein provided can be obtained.

Accordingly, a genuine need exists for a method for producing a Xanthomonas heteropolysaccharide which can be readily filtered and separated from other debris in the solution such as bacterial cells and proteinaceous material. Moreover a need exists for a heteropolysaccharide which can be injected into porous media such an oil-bearing sandstone formations, and which can be added to foodstuffs or pharmaceutical preparations without discoloring or markedly changing the clarity of such preparations.

SUMMARY OF THE INVENTION

As one embodiment of the invention there is provided a composition containing a heteropolysaccharide produced by the action of bacteria of the genus Xanthomonas, wherein the heteropolysaccharide has been modified such that the modified heteropolysaccharide is capable of imparting a viscosity of at least 4.0 centipoises to an aqueous test solution containing 2 wt. % NaCl and 0.2 wt. % $CaCl_2$ when said modified heteropolysaccharide is added to said solution at a concentration of approximately 600 parts per million, by weight, as measured on a Brookfield viscosimeter with a UL adapter at 60 rpm at 25° C. and said modified heteropolysaccharide is further capable of imparting a filterability such that more than 1000 ml. of a different aqueous test solution containing 8.8 wt. % salt comprised of NaCl and $CaCl_2$ on a 10:1 weight ratio (i.e., 8% NaCl and 0.8% $CaCl_2$) and approximately 600 parts per million concentration, by weight, of said modified heteropolysaccharide will pass without plugging through a Millipore ® filter having a diameter of 13 mm and a pore size of 5 microns at a constant pressure drop of about 1.55 psig.

The modified heteropolysaccharide of the present invention is also characterized as capable of imparting an Effective Viscosity of less than 5 to an aqueous test solution containing 2 wt. % NaCl and 0.2 wt. % $CaCl_2$ at about 22° C. when said modified heteropolysaccharide is added to said test solution at a concentration of approximately 600 parts per million, by weight, and passed through a Nuclepore ® filter having a pore size of 1 micron. The "Effective Viscosity" is defined as the ratio of the normalized slope of the pressure drop-flow rate curve at a given filter size for the test solution containing the salt and heteropolysaccharide divided by the slope of the curve for distilled water under the same test conditions. The "Effective Viscosity" normalizes the measured pressure drop values to remove differences which are due to variations in number of filter pores and in filter pore geometry. A sharply higher value for Effective Viscosity for a heteropolysaccharide-containing solution compared to the value obtained for a second solution in passing through the same sized filter is indicative that the first solution contains heteropolysaccharide having a larger average particle size than the heteropolysaccharide in the second test solution.

The filterability test as set forth above is also a means for describing the improved injectivity properties of the modified heteropolysaccharide of the present invention, particularly when the modified heteropolysaccharide is put to use in the recovery of oil from subterranean formations.

As another embodiment of the present invention there is provided a process for preparing the improved heteropolysaccharides by a process comprising the steps:

(a) preparing an aqueous solution containing from about 200 to about 30,000 parts per million, by weight, of a heteropolysaccharide fermentation product produced by the action of bacteria of the genus Xanthomonas and at least about 0.5 weight percent of at least one salt, preferably from 0.5 to about 10 weight percent inorganic salts selected from the group consisting of sodium chloride, calcium chloride and mixtures thereof to obtain a saline heteropolysaccharide solution;

(b) heating said saline heteropolysaccharide solution to a temperature of at least about 100° C., preferably in the range from about 100° C. to about 180° C.;

(c) maintaining said saline heteropolysaccharide solution at a temperature of at least about 100° C., preferably for a period of time sufficient to improve the filterability characteristics but not so long that the viscosity-imparting properties of the saline-heat treated heteropolysaccharide are substantially impaired, e.g., from about 1 to about 300 minutes.

In still another embodiment of the present invention there is provided a process for recovering oil from a subterranean formation penetrated by at least one injection well and at least one production well by injecting into said injection well and into said subterranean formation an aqueous solution containing a heteropolysaccharide produced by the action of bacteria of the genus Xanthomonas, wherein the heteropolysaccharide has been modified such that the modified heteropolysaccharide is capable of imparting a viscosity of at least 4.0 centipoises to an aqueous test solution containing 2 wt. % NaCl and 0.2 wt. % $CaCl_2$ when said modified heteropolysaccharide is added to said test solution at a concentration of approximately 600 parts per million, by weight, as measured on a Brookfield viscosimeter with a UL adapter at 60 rpm at 25° C. and said modified heteropolysaccharide is further capable of imparting a filterability such that more than 1000 ml of a different aqueous test solution containing 8.8 wt. % salt comprised of NaCl and $CaCl_2$ at a 10:1 weight ratio and approximately 600 parts per million concentration, by weight, of said modified heteropolysaccharide will pass through a 13 mm diameter Millipore ® filter having a pore size of 5 microns at a constant pressure drop of about 1.55 psig with plugging. Preferably the modified heteropolysaccharide will be such that it is capable of imparting an Effective Viscosity of less than 5 to an aqueous test solution containing 2 wt. % of NaCl and 0.2 wt. % $CaCl_2$ at about 22° C. when said modified heteropolysaccharide is added to said test solution at a concentration of approximately 600 parts per million, by weight, and passed through a Nuclepore ® filter having a pore size of 1 micron.

The heteropolysaccharide that has been subject to the above-described saline heat treatment is more readily separated from debris in the solution, such as bacterial cells and proteinaceous material, by filtration or other separation means. The saline heat treated heteropolysaccharide is physically different from a heteropolysaccharide which has not been subjected to such treatment. Tests demonstrate that the treatment results in a reduction in average particle size.

The heteropolysaccharide which has been subjected to the saline heat treatment and separated from the debris in the heteropolysaccharide solution can be employed in aqueous solutions to recover oil from subterranean formations. It can be injected into such formations without serious plugging of the porous medium. Such heteropolysaccharide may also be used in foodstuffs, beverages, cosmetics, pharmaceutical preparations, etc.

DESCRIPTION OF THE PREFERRED EMBODIMENTS

In addition to the above-described characterizing features of the modified heteropolysaccharides of the present invention, these modified heteropolysaccharides are differentiated from native, unmodified heteropolysaccharides produced by bacteria of the genus Xanthomonas by all the following criteria:

A. Election microscopy of individual molecules shows that native unmodified heteropolysaccharide molecules are 2 to 10 μm long, 4 nm thick and unbranched, whereas the modified heteropolysaccharide molecules of the present invention are only 1–2 μm long but remain 4 nm thick. In other words, the individual molecules of the modified heteropolysaccharides of the present invention are shorter than native, unmodified heteropolysaccharide.

B. Sedimentation by ultracentrifugation shows that for native, unmodified heteropolysaccharide, the average sedimentation coefficient is about $16-20 \times 10^{-13}$ sec whereas the modified heteropolysaccharides of the present invention exhibit an average sedimentation coefficient of less than about $15.5 \times 10^{-13}$ sec and generally less than about $12 \times 10^{-13}$ sec.

Moreover, more than 10% by weight, of the unmodified, native heteropolysaccharide has a sedimentation coefficient exceeding $25 \times 10^{-13}$ sec, whereas for the modified heteropolysaccharide of the present invention considerably less than 10%, by weight, of the heteropolysaccharide has sedimentation coefficient exceeding $25 \times 10^{-13}$ sec.

C. Membrane partition chromatograms, in which the heteropolysaccharide molecules flow through Nucelpore ® membranes of known pore size, show that native, unmodified heteropolysaccharide molecules have a mean hydrodynamic diameter of 0.6 μm, whereas the modified heteropolysaccharide molecules of the present invention have a hydrodynamic diameter of 0.6 μm, whereas the modified heteropolysaccharide molecules of the present invention have a hydrodynamic diameter of less than about 0.4 μm with many particles of much smaller size.

D. The chemical composition of the modified heteropolysaccharide of the present invention is distinct from the native, unmodified heteropolysaccharide derived from Xanthomonas in that:

(i) precipitation of the modified heteropolysaccharide of the present invention by the action of trivalent ions such as $Fe^{+3}$, or by cetyltrimethylammonium bromide precipitating agents, in the presence of $CaCl_2$, or NaCl respectively, is less than that for native, unmodified heteropolysaccharide at the same level of $CaCl_2$ or NaCl. For example, the modified heteropolysaccharide of the present invention requires less NaCl (as a precipitating protective agent) than required for the native, unmodified heteropolysaccharide at the same level of cetyltrimethylammonium bromide precipitating agent. As another illustration of this distinction, substantially more $FeCl_3$ is required to precipitate the modified heteropolysaccharide of the present invention than native, unmodified heteropolysaccharide at the same level of $CaCl_2$. This result suggests that the modified heteropolysaccharide of the present invention has fewer negatively charged groups per unit length than native, unmodified Xanthomonas-produced heteropolysaccharide;

(ii) The modified heteropolysaccharide of the present invention contains fewer acetyl groups per gram of heteropolysaccharide than native, unmodified heteropolysaccharide, e.g., about 10% fewer acetyl groups per gram than for the native heteropolysaccharide; and (iii) The modified heteropolysaccharide of the present invention contains fewer pyruvate groups per gram than native, unmodified heteropolysaccharide, e.g., about 20% fewer pyruvate groups per gram than the native heteropolysaccharide.

It is apparent from the above, that the modified Xanthomonas heteropolysaccharides not only have improved injectivity properties, but are chemically and physically modified in a manner which is distinct from native, unmodified Xanthomonas heteropolysaccharides.

Accordingly, this invention provides an improved modified heteropolysaccharide formed by bacteria of the genus Xanthomonas which can be readily separated from bacterial cells, proteinaceous matter, and other debris resulting from the process of making such heteropolysaccharides and possesses a larger proportion of smaller molecular weight molecules than the native, unmodified heteropolysaccharides as evidenced by electron microscopy, ultracentrifuge sedimentation coefficient and membrane partition chromatograms. Another important characteristic of the modified heteropolysaccharide composition of the present invention is the relative absence of very high molecular weight heteropolysaccharide molecules compared to the native, unmodified heteropolysaccharide. As a result, a heteropolysaccharide is obtained which can be readily injected into subterranean formations in aqueous solutions and which can be added to foodstuffs, beverages, cosmetics, and pharmaceuticals without discoloring them or materially changing their clarity. As will be described in greater detail herein, this improved heteropolysaccharide is a result of a saline, heat-treating process which is applied during any stage of the manufacturing process subsequent to the formation of the heteropolysaccharide, or alternatively may be applied to dried, commercially available Xanthomonas heteropolysaccharide. The process can be applied at a plant site where Xanthomonas heteropolysaccharides are manufactured or it can be applied at a field location prior to injecting the Xanthomonas heteropolysaccharide solution into a subterranean formation for oil recovery, when desired.

The following is a general description or illustration of the process for manufacturing heteropolysaccharides and describes the saline heat treatment of this application in such a process.

The heteropolysaccharides which are used in the practice of this invention are generally fermentation products produced by the action of bacteria of the genus Xanthomonas upon carbohydrates. Representative species of these bacteria include *Xanthomonas campestris, Xanthomonas phaseoli, Xanthomonas malvacearum, Xanthomonas carotae, Xanthomonas translucens, Xanthomonas hederae, Xanthomonas papavericola, Xanthomonas begoniae,* and *Xanthomonas incanae.* Studies have shown that the production of the heteropolysaccharides is a characteristic trait of members of the genus Xanthomonas but that certain xanthomonas synthesize such heteropolysaccharides with particular efficiency and are therefore more attractive for purposes of the invention than are others. *Xanthomonas campestris, Xanthomonas begoniae,* and *Xanthomonas incanae* are outstanding in this respect and hence are preferred species.

A variety of carbohydrates may be fermented by means of the Xanthomonas organisms to produce the heteropolysaccharides. Suitable carbohydrates include glucose, sucrose, fructose, maltose, lactose, galactose, soluble starch, and the like. Since such carbohydrates need not be in a refined state, many crude products having a high carbohydrate concentration may be utilized. Specific examples include raw sugar, crude molasses, and the like. Unrefined carbohydrate sources such as these are normally much less expensive than the refined products and are therefore preferred for purposes of the invention.

The heteropolysaccharide is normally produced from the carbohydrates described above by employing an aqueous fermentation medium containing from about 1 to about 5 percent by weight of a suitable carbohydrate, from about 0.01 to about 0.5 percent by weight of dipotassium acid phosphate, and from about 0.1 to about 10 percent by weight of a nutrient including organic nitrogen sources and appropriate trace elements. The nutrient utilized will normally be a by-product material such as distillers' solubles. "Stimuflav," marketed by Hiram Walker & Sons, is a commercially marketed nutrient prepared from distillers' solubles. A mixture containing 2 weight percent raw sugar, 0.1 weight percent dipotassium acid phosphate and 0.5 weight percent "Stimuflav" has been found to yield particularly good results. It will be understood that fermentation media containing other ingredients may be most effective when the ingredients are combined in slightly different proportions.

The fermentation reaction is carried out by first sterilizing a medium of the type described above and then inoculating it with organisms of the genus Xanthomonas. The fermentation medium is prepared by adding a carbohydrate source such as raw sugar, water, the nitrogen source and a buffering agent to a suitable mixing tank. The fermentation medium is then withdrawn from the mixing tank by means of suitable piping and valves, and pumped to a sterilization unit. A typical sterilization unit might be a vat provided with an electrical heater or similar apparatus within which the fermentation medium can be heated to a temperature of from about 95° C. to about 135° C. and held at that temperature for a period of from about 2 to about 5 minutes or longer. Higher temperatures and longer residence times may be employed if desired but in general the temperatures and times indicated will be sufficient to kill any bacteria present in the fermentation medium and render it sterile. A sterile fermentation medium is then withdrawn and passed to a cooling unit to reduce the temperature of the medium to a point between 24° C. and 38° C., preferably to a temperature between 24° C. and 30° C. The cooled, sterile medium is then discharged into a fermentation vessel.

An inoculum of Xanthomonas organism is introduced into the fermentation vessel to effect the fermentation reaction. The inoculum is prepared in a preparation tank which is provided with an agitator. The inoculum is prepared by permitting the bacteria to grow on a small amount of the fermentation medium previously sterilized within the preparation tank by bubbling steam into it. Sterilized air, necessary for the growth of the bacteria, is also introduced into the preparation tank. The inoculum is provided with gentle agitation during the incubation period. The rate at which the inoculum is produced is controlled in order to maintain a steady supply for use in the main fermentation process. The inoculum thus prepared is then introduced with the fermentation medium into a fermentation vessel.

Sterilized air is introduced into the fermentation vessel to provide aerobic conditions necessary for the fermentation of the sterile medium by the bacteria. A sparger distribution plate or similar device is located in the lower part of the fermentation vessel in order to assure effective contact between the air and the fermentation medium. Gentle agitation can be provided by means, such as a propeller agitator, located in the main fermentation vessel. The pH of the solution during fermentation is generally held between about 6 and about 7.5 by the addition of a suitable base such as sodium hydroxide or by a buffer such as dipotassium acid phosphate. This pH control generally results in substantially higher yields of heteropolysaccharides by controlling acidic byproducts of the fermentation which can cause the fermentation to stop short of completion.

Fermentation is normally carried out for a period of from 2 to 3 days or longer. At the end of this time an aqueous solution of heteropolysaccharide formed by the action of the bacteria upon the sugar results. This solution normally contains from about 0.5 to about 3 weight percent of the heteropolysaccharide and generally has a viscosity between about 500 and 50,000 centipoises.

The heteropolysaccharide thus produced is a "native, unmodified heteropolysaccharide" as referred to herein.

The foregoing is a general description of the common fermentation reaction of bacteria of the genus Xanthomonas and carbohydrates. However, it will be recognized by those skilled in the art that sources of carbon other than carbohydrates may be employed. Typical carbon sources include methanol, ethanol, acetates, and paraffinic hydrocarbons in a pure or crude state, such as kerosine.

The saline heat treating process may be applied to such a fermentation broth or beer or at any other stage of the manufacturing process subsequent to the formation of the heteropolysaccharide (i.e., the "native, unmodified heteropolysaccharide"). The salinity of the solution is adjusted to bring the salt concentration to a level of about 0.5 wt. % or higher. For reasons not completely understood, these salts protect the heteropolysaccharide from thermal degradation during heat treating. Salt concentrations as low as 0.5 wt % have been found effective, although salt concentrations on the order of 2 wt. % are generally preferred. Higher salt concentrations, up to the solubility limit of salt in the fermentation broth, do not adversely affect the solution. However, salt concentrations in excess of the solubility limit can, of course, interfere with the separation of the heteropolysaccharide from other components of the fermentation solution. Generally, it will be preferred to maintain the salt concentration at a level below 10 wt. % to avoid precipitation of inorganic salts and to avoid phase separation of the fermentation solution.

The salt solution employed in the saline heat treating can be any one of a number of readily available and inexpensive substances. Inorganic salts containing sodium, calcium, magnesium, potassium, and barium as a cation and chloride, sulfate, carbonate, bicarbonate, and phosphate as an anion are suitable in the practice of this invention. However, salts such as sodium chloride and calcium chloride are generally preferred since they are readily available, relatively inexpensive and are compatible with most subterranean formations which is desirable when the polymer is to be used for oil recovery purposes. The salt chosen for use in this invention should, of course, be soluble to the desired level at the treatment temperature and should be stable. The salt should not be highly corrosive, toxic, or detrimental to the polymer in the solution. In the final analysis, the salt should be capable of protecting the polymer from degradation during heating. Simple viscosity measurements will enable one skilled in the art to determine whether a given salt is adequately performing this function.

During the saline heat treatment step, thermal energy at a given level and for a given period of time is applied to the heteropolysaccharide-containing solution. In practical applications, the temperature will be in the range of 100° C. to 180° C. and the temperature will be maintained within this range for a time period of from 1 to 300 minutes. This heating can be accomplished by means of steam coils, steam injection or electric heaters within the fermentation vessel or a subsequent transfer vessel. The heat treatment level and heat treatment length are, of course, interrelated. If the treatment length is relatively short or the temperature is relatively low, the filtration characteristics of the heteropolysaccharide will be less desirable; conversely, if the treatment length is relatively long or the temperature level is relatively high, the viscosity imparting properties of the heteropolysaccharide product will be decreased. Thus, in its broadest sense, the temperature level and the duration of the thermal treatment are interrelated through the filterability of the product and its viscosity imparting properties. These two process variables—temperature and time—can be easily adjusted by one skilled in the art by simply testing the filterability of the product and by testing the viscosity imparting properties of the product.

It may be desirable to mechanically shear the heteropolysaccharide solution either before or after it has been subjected to the saline heat treatment. This shear can be conveniently imposed on the solution by a mechanical agitator, passing the solution through an orifice plate or other conventional means. Such shearing is not essential to the practice of this invention, but it assists in assuring that the components of the solution are totally solubilized, and it aids in subsequent operations.

Upon completion of the saline heat treatment, the crude heteropolysaccharide can be separated from the bacterial cells by centrifugation or filtration, if desired. Precipitation with methanol, ethanol, isopropanol, acetone, or similar agents permits the isolation of a relatively pure heteropolysaccharide. This latter step is not essential in the preparation of the improved thickening agent of this invention, however, and can be omitted if desired.

Upon completion of the saline heat treatment, if desired, a biocide may be added. The biocide is not essential to the practice of the invention but does protect the polymer solution from microbial degradation and improves its shelf life. Such biocides include any of a great variety known to the art, for example, sodium trichlorophenate; 2,2-dibromo-3-nitrilpropionamide; 1-(3-chlorallyl)-3,5,7-triaza-1-azonia adamantane chloride; sodium O-phenylphenate; mixtures of sodium pentachlorophenate and sodium salts of other chlorophenols; sodium 2-pyridinethiol 1-oxide; zinc 2-pyridinethiol 1-oxide; mixtures of sodium 2-pyridinethiol 1-oxide and 2,2-dithio-bis (pyridine-1-oxide); mixtures of sodium trichlorophenate and methanol; formaldehyde and formalin solutions.

If the biocide to be used is heat-stable and will withstand the conditions of the particular saline heat treatment to be used, it may, if desired, be added to the heteropolysaccharide solution prior to the heat treatment step. Alternatively, biocide addition may be made after any desired dilution of the heat treated heteropolysaccharide solution has been accomplished.

Heat treating in a saline solution with subsequent filtration can be incorporated in the process steps for producing commercial grade heteropolysaccharide or alternatively, commercial grade heteropolysaccharide can be produced and then subjected to the treating process of this invention. For example, commercially available heteropolysaccharide can be obtained from a number of sources such as the products sold under the tradename Kelzan XC by Kelco Company. The commercial grade heteropolysaccharide is dissolved in water in a concentration of 200 to 30,000 parts per million in distilled water with the addition of from 0.5 to 10 weight percent salts. This solution is heated to a temperature ranging from 100° C. to 180° C. for a period of time ranging from 1 to 300 minutes. The heteropolysaccharide solution can then be subjected to mechanical separation to remove all entrained residual material such as clumps of incompletely solubilized heteropolysaccharide residual proteinaceous material, and residual whole bacterial cells or other cellular debris.

It will be understood that the foregoing description is directed to a specific process for preparing the improved thickening agent of this invention and that the invention itself is not limited to the precise reagents and apparatus described. The process described is essentially a batch type operation and can be obviously converted into a continuous one by continuously introducing sterile medium into, and withdrawing fermentate from, the fermentation vessel, heat treating by means of a flow-through heat exchanger with appropriate residence times, and by making other minor modifications. It will be recognized that instrumentation, steam lines, and other features conventional in the process such as that described above have not been set forth in full detail. Such features will be familiar to those skilled in the art and need not be specifically described in order to permit a full understanding of the invention.

The process of this invention can be further illustrated by reference to the results obtained in a series of experiments wherein the heteropolysaccharides prepared in accordance with the teachings of this invention are tested to determine their effectiveness particularly as compared with other thickening agents. For the purpose of clarity and for the purpose of isolating process variables, the experiments set forth in the following examples were conducted using heteropolysaccharides produced in accordance with the teaching of the prior art. The heteropolysaccharides used in the experiments set forth in these examples are, in the main, commercially available materials and clearly demonstrate the effectiveness of the saline heat treating process of this invention to such commercially available products. However, it will be appreciated by those skilled in the art that the information to be derived from these examples can be equally applied to treatment of the fermentate broth or beer as previously discussed.

EXAMPLE I

Example I illustrates the saline heat treating process as applied to a commercially available heteropolysaccharide (the heteropolysaccharide used is sold under the tradename Kelzan ® XC). This heteropolysaccharide and a biocide were added to two liters of water and dissolved. The heteropolysaccharide was added at a concentration of 3000 ppm. The biocide was a trichlorophenol in an alcohol/water solution sold under the tradename Corexit 7671 by Exxon Chemical Company, USA. The biocide was added at a concentration of 2000 ppm. As will be subsequently discussed, the biocide is not essential to the practice of the invention but does protect the heteropolysaccharide from degradation and improves its shelf life.

This mixture was thoroughly hydrated by stirring with a magnetic stirrer for 18 or more hours. Subsequent to this hydration, the salt concentration of the solution was increased to approximately 2.2 weight percent by adding 40 grams of sodium chloride and 4.0 grams of calcium chloride. The saline heteropolysaccharide solution was then stirred for an additional two hours with the magnetic stirrer to insure proper solution of the added salts. The solution was then separated into five-hundred milliliter batches for convenience in handling and subjected to shear by placing the batches in a Waring Blendor ® at 19,000 rpm for three minutes. This shearing is not essential to the practice of the invention but assists in assuring that the components of the solution are totally solubilized.

The sheared samples were then heat treated in an autoclave. In this heat treating, a 500 ml batch was placed in a flask which was tightly capped with aluminum foil and Saran Wrap ® and heated in the autoclave at a temperature of 121° C. for one hour. After this heat treatment, the flask was cooled to room temperature. The solution was vacuum prefiltered at a pressure drop of 28" of water through a 47 mm diameter AP25 Millipore ® prefiltration pad to remove larger particulate material. The solution was again mixed for one minute in a Waring Blendor ® at 19,000 rpm. The solution was then subjected to a step-wise filtration procedure by vacuum filtering (28" of water) the solution through a series of 4 Millipore ® filters. The Millipore ® filters used in the filtration process were all 47 mm in diameter and had average pore sizes of 1.2, 0.8, 0.65, and 0.45 microns. This filtered solution was then used to prepare 600 ppm heteropolysaccharide solutions containing 8.8% salts by making a 1:4 dilution with a solution containing 9.5% sodium chloride and 0.95% calcium chloride. Subsequently, the effluents were subjected to tests for viscosity and injectability. The viscosity measurements were made using a Brookfield viscosimeter at 25° C. and 60 rpm using a UL adapter. The filtration tests were conducted by flowing the samples in one liter batches through 13 mm diameter, 5 micron Millipore ® filters at a pressure drop of 1.55 psi to measure injectivity, flow rates, and total throughput.

EXAMPLE II

Example II illustrates the superior filterability of the saline heat treated heteropolysaccharide compared to unheated heteropolysaccharide. Flasks containing 3000 ppm heteropolysaccharide were prepared by dissolving 1.5 grams of Kelzan XC ® in 500 ml of distilled water by overnight stirring with a magnetic stirring bar at room temperature. To this concentrate were added 10 grams of NaCl and 1.0 grams of $CaCl_2$ and the mixture was stirred to dissolve the salts (2.2% salts). The flasks were capped tightly with aluminum foil and Saran Wrap ® and then heated in an autoclave at 121° C. for various periods of time, as indicated in Table 1. After saline heat treatment, the flasks were cooled to room temperature and the 3000 ppm concentrates were sheared in a Waring Blendor ® at 19,000 rpm for 3 minutes.

The sheared 3000 ppm concentrates were then used to prepare 600 ppm heteropolysaccharide solutions containing 8.8% salts by making a 1:4 dilution with water containing 9.5% NaCl and 0.95% $CaCl_2$. The 600 ppm solutions were vacuum prefiltered sequentially through 47 mm diameter AP25 Millipore ® prefiltration pads and $14\mu$ and $5\mu$ Millipore ® filters. All solutions were adjusted to pH 7.0 with 0.1 N NaOH. Viscosity measurements were made using a Brookfield viscosimeter at 25° C. and 60 rpm using a UL adaptor.

As a measure of injectivity, a filtration test, well-known and well-accepted in the art, was used. The flow rates and total throughput through 13 mm diameter, $5\mu$ Millipore ® filters at a pressure drop of 1.55 psi were measured. The viscosities, flow rates and total throughputs of solutions prepared from untreated and thermally treated material are shown in Table 1. The Millipore ® filters used in this Example and referred to throughout this application were Millipore ® type MF, which are well known for use in filtering aqueous solutions.

TABLE 1
EFFECT OF SALINE HEAT TREATMENT AT 121° C. ON VISCOSITY AND FILTERABILITY OF HETEROPOLYSACCHARIDE SOLUTIONS IN 8.8% BRINE

| Saline Heat Treatment Time (Hrs @ 121° C.)[a] | Viscosity[b] (cp) | Filterability[b] | | Remarks |
|---|---|---|---|---|
| | | Flow rate (ml/min)[c] | | |
| | | @ 100 ml | @ 1000 ml | |
| Untreated | 5.9 | — | — | Filter plugged at 32 ml |
| 1.0 | 6.2 | 3.9 | — | Filter plugged at 490 ml |
| 1.5 | 6.2 | 3.9 | — | Filter plugged at 630 ml |
| 3.0 | 6.0 | 8.3 | 2.8 | More than 1000 ml throughput without plugging |
| 4.0 | 5.3 | 11.0 | 3.8 | More than 1000 ml throughput without plugging |
| 5.0 | 4.6 | 12.5 | 4.2 | More than 1000 ml throughput without plugging |

[a]Saline heat treatment was done using 3,000 ppm heteropolysaccharide concentrates in 2.2% brine.
[b]Filterability and viscosity measurements were done on the 600 ppm heteropolysaccharide solutions in 8.8% brine.
[c]Flow rates are shown for the points at which 100 or 1000 ml of solution had passed through the filter.

The date in Table 1 clearly demonstrate the marked improvement in flow characteristics of solutions prepared from saline heat treated material (the modified heteropolysaccharides of the present invention) when compared to solutions prepared from untreated or unmodified samples. When the concentrates were heated at 121° C. for 1–1.5 hours, the resultant solutions exhibited improved initial flow rates over the untreated or unmodified material, and there was a considerably higher total throughput. Saline heat treatment at 121° C. for 3–5 hours resulted in heteropolysaccharide solutions that filtered very much more rapidly and with greatly increased total throughputs. Moreover, the viscosity of the solutions prepared from the 3-hour saline heat treated material was completely unimpaired; the 4- and 5-hour saline heat treated samples had somewhat lower viscosities.

EXAMPLE III

This Example III demonstrates the superior injectivity and throughput of the modified heteropolysaccharide compositions prepared in the manner of the present invention compared to heteropolysaccharide compositions prepared in accordance with the teachings of U.S. Pat. No. 3,729,460 to Patton.

A concentrate containing heteropolysaccharide was prepared and treated as in Example I for one hour at 121° C. This treated sample of heteropolysaccharide contained 600 ppm Kelzan XC ® and 100 ppm Corexit 7671 in 8.8% brine. A second sample of heteropolysaccharide (Kelzan XC ®) was subjected to the alkaline heating process disclosed in U.S. Pat. No. 3,729,460 at column 5, lines 60-74. This second sample was then sheared in a Waring Blendor ® for three minutes at a rate of 19,000 rpm and finally diluted to a concentration of 600 ppm heteropolysaccharide in 8.8% brine. Table 2 shows the comparative effect of saline heat treating to alkaline heat treating and the superiority of saline heat treated material on filterability.

TABLE 2

COMPARISON OF SALINE HEAT TREATING TO ALKALINE HEAT TREATING

| Sample | Filterability Flow Rate (ml/min) | | Remarks |
|---|---|---|---|
|  | @ 100 ml | @ 1000 ml |  |
| Alkaline heat treated | 7.0 | 0 | Filter plugged at 560 ml |
| Saline heat treating | 13.0 | 9.0 | More than 1000 ml throughput without plugging |

As can be seen from the data presented in Table 2, the modified heteropolysaccharide produced by the saline heat treating of the present invention shows markedly superior injectability properties compared to the alkaline heat treating of the prior art. The flow rate in milliliters per minute is consistently higher for the modified heteropolysaccharide prepared in accordance with the present invention and an appreciably greater quantity of this modified heteropolysaccharide can be passed through the filter without plugging, e.g., more than 1000 ml.

EXAMPLE IV

Example IV illustrates the high degree of clarification that can be achieved by the modified heteropolysaccharides of the present invention. Solutions of Kelzan XC ® heteropolysaccharide were prepared by dissolving the heteropolysaccharide in distilled water at a concentration of 3000 ppm. One of the samples contained a biocide, Corexit 7671, in a concentration of 2000 ppm and both samples contained 2.2 wt. % salt. Both samples were subjected to the saline heat treating process described in Example II for one hour at 121° C. The treated 3000 ppm concentrates were vacuum filtered through the following series of 47 mm diameter Millipore ® filters: AP-25; 1.2μ; 0.8μ; 0.65μ; and 0.45μ. Table 3 shows the percent transmission at a wave length of 610 millimicrons against a blank of distilled water in a one centimeter cell as measured by a spectrophotometer.

TABLE 3

CLARIFICATION OF SALINE HEAT TREATED SOLUTIONS, WITH AND WITHOUT BIOCIDE

| Treatment Stage | Percent Transmission Compared to Distilled Water | |
|---|---|---|
|  | 3000 ppm Heteropolysaccharide 2000 ppm Corexit 7671 2.2% brine | 3000 ppm Heteropolysaccharide 2.2% brine |
| Following hydration | 28% | 44% |
| Following shear for 3 minutes at 19,000 rpm, Waring Blender | 28% | 44% |
| After 1 hr. heat treatment, 131° C. | 28% | 44% |
| Prefiltration, Millipore AP-25 ® | 38% | 81% |
| Filtration, 1.2 micron Millipore ® | 49% | 93% |
| Filtration, 0.8 micron Millipore ® | 74% | 96% |
| Filtration, 0.65 micron Millipore ® | 96% | 100% |
| Filtration, 0.45 micron Millipore ® | 100% | 100% |

Table 3 shows that the process of this invention enables one to obtain solutions of Xanthomonas heteropolysaccharide which have the clarity of distilled water.

EXAMPLE V

A series of tests were carried out in order to compare the effect of time and temperature of the saline heat treatment on the viscosity and injectivity of solutions of treated polymer. Xanthomonas heteropolysaccharide concentrates were prepared and treated as in Example II.

Tables 4 and 5 compare the effect of time and temperature on the viscosity and injectivity of the modified heteropolysaccharide containing solutions.

The data in Tables 4 and 5 show that temperature and holding times may be varied to give the desired results. Excellent flow rates and unimpaired viscosities were observed with solutions prepared from samples heated for 16 minutes at 128° C. (Table 4) or for 8 minutes at 135° C. (Table 5). Even greater flow rates were observed with samples heated for longer times at these temperatures, but there was some loss in viscosity.

TABLE 4

EFFECT OF SALINE HEAT TREATMENT AT 128° C. ON VISCOSITY AND FILTERABILITY OF HETEROPOLYSACCHARIDE SOLUTIONS IN 8.8% BRINE

| Thermal Treatment Time (Min @ 128° C.)[a] | Viscosity[b] (cp) | Filterability[b] Flow Rate (ml/min)[c] | | Remarks |
|---|---|---|---|---|
|  |  | @ 100 ml | @ 1000 ml |  |
| Untreated | 5.9 | — | — | Filter plugged at 32 ml |
| 16 | 6.0 | 4.6 | 1.5 | More than 1000 ml throughput without plugging |
| 32 | 5.5 | 9.7 | 6.4 | More than 1000 ml throughput without plugging |
| 45 | 4.9 | 15.2 | 11.4 | More than 1000 ml throughput without plugging |
| 60 | 4.3 | 18.0 | 12.5 | More than 1000 ml throughput |

TABLE 4-continued
EFFECT OF SALINE HEAT TREATMENT AT 128° C. ON VISCOSITY AND FILTERABILITY OF HETEROPOLYSACCHARIDE SOLUTIONS IN 8.8% BRINE

| Thermal Treatment Time (Min @ 128° C.)[a] | Viscosity[b] (cp) | Filterability[b] Flow Rate (ml/min)[c] @ 100 ml | @ 1000 ml | Remarks |
|---|---|---|---|---|
| | | | | without plugging |

[a]Saline heat treatment was done using 3,000 ppm heteropolysaccharide concentrates in 2.2% brine.
[b]Filterability and viscosity measurements were done on the 600 ppm heteropolysaccharide solutions in 8.8% brine.
[c]Flow rates are shown for the points at which 100 or 1000 ml of solution had passed through the filter.

TABLE 5
EFFECT OF SALINE HEAT TREATMENT AT 135° C. ON VISCOSITY AND FILTERABILITY OF HETEROPOLYSACCHARIDE SOLUTIONS IN 8.8% BRINE

| Thermal Treatment Time (Min @ 135° C.)[a] | Viscosity (cp) | Filterability[b] Flow Rate (ml/min)[c] @ 100 ml | @ 1000 ml | Remarks |
|---|---|---|---|---|
| Untreated | 5.9 | — | — | Filter plugged at 32 ml |
| 8 | 5.85 | 5.7 | 3.7 | More than 1000 ml throughput without plugging |
| 16 | 5.0 | 7.5 | 4.0 | More than 1000 ml throughput without plugging |
| 24 | 4.25 | 11.0 | 6.5 | More than 1000 ml throughput without plugging |
| 32 | 3.50 | 17.0 | 13.0 | More than 1000 ml throughput without plugging |

[a]Saline heat treatment was done using 3,000 ppm heteropolysaccharide concentrates in 2.2% brine.
[b]Filterability and viscosity measurements were done on the 600 ppm heteropolysaccharide solutions in 8.8% brine.
[c]Flow rates are shown for the points at which 100 or 1,000 ml of solution had passed through the filter.

EXAMPLE VI

A series of tests were carried out in order to determine the effect of the saline heat treatment on a variety of commercially available Xanthomonas heteropolysaccharide samples. Duplicate flasks with each set containing 3000 ppm of one of six commercially available polymer were prepared as in Example II. The samples used were as follows:

| | |
|---|---|
| (A) Kelzan ®: | The standard industrial grade heteropolysaccharide suitable for most industrial applications. Kelco Co., San Diego, California |
| (B) Kelzan XC ®: | An industrial grade heteropolysaccharide of particular value as an additive to oil well drilling mud. Kelco Co., San Diego, California. |
| (C) Kelzan MF ®: | An industrial grade heteropolysaccharide for secondary and tertiary oil recovery. Kelco Co., San Diego, California |
| (D) Kelzan ®: | Same as (A) but a different batch. |
| (E) SS-3192: | Laboratory sample of highly purified heteropolysaccharide. Kelco Co., San Diego, California. |
| (F) XB-23: | Xanthomonas heteropolysaccharide. General Mills Chemical Inc., Minneapolis, Minnesota. |

One set of flasks was heated as in Example II at 121° C. for 3 hours, and then cooled to room temperature; the second set received no heat treatment. In the cases of samples E and F, a third set of flasks was treated for 1 hour instead of for 3 hours. The 3000 ppm concentrates were sheared in a Waring Blendor ® at full power for three minutes and were used to prepare 600 ppm solutions in 8.8% and in 1.76% brine by making a 1:4 dilution with water containing 1.5% NaCl and 0.15% $CaCl_2$. The results of viscosity and filtration tests in 8.8% brine are shown in Table 6, and show that the method of the present invention can be applied to a wide variety of Xanthomonas heteropolysaccharide samples, ranging from rather crude to very pure preparations, and from different manufacturers.

The data for viscosity and for injectivity tests in 1.76% brine are shown in Table 7, and show that the method of the present invention improves injectivity characteristics in low salt as well as in high salt concentrations.

TABLE 6
EFFECT OF SALINE HEAT TREATMENT AT 121° C. ON VISCOSITY AND FILTERABILITY OF VARIOUS HETEROPOLYSACCHARIDE SOLUTIONS IN 8.8% BRINE[a]

| | Vis.[b] (cp) | Filterability[b] Flow Rate (ml/min)[c] @ 100 ml | @ 1000 ml | Remarks |
|---|---|---|---|---|
| Sample A | | | | |
| Untreated | 5.85 | — | — | Filtered plugged at 35 ml |
| Treated-3 hours | 5.35 | 16.0 | 5.6 | More than 1000 ml throughput without plugging |
| Sample B | | | | |
| Untreated | 5.35 | — | — | Filter plugged at 50 ml |
| Treated-3 hours | 4.95 | 15.5 | 2.7 | More than 1000 ml throughput without plugging |
| Sample C | | | | |
| Untreated | 5.75 | — | — | Filter plugged at 44 ml |
| Treated-3 hours | 5.60 | 12.5 | 2.5 | More than 1000 ml throughput without plugging |
| Sample D | | | | |
| Untreated | 6.05 | — | — | Filter plugged at 30 ml |
| Treated-3 hours | 5.50 | 14.5 | 2.4 | More than 1000 ml throughput without plugging |
| Sample E | | | | |
| Untreated | 4.65 | — | — | Filter plugged at 54 ml |
| Treated-3 hours | 3.40 | 17.0 | 13.0 | More than 1000 ml throughput without plugging |
| Treated-1 hour | 4.65 | 13.8 | 12.0 | Filter plugged at 54 ml More than 1000 ml throughput without plugging |
| Sample F | | | | |
| Untreated | 5.35 | — | — | Filter plugged at 12 ml |
| Treated-3 hours | 3.40 | 12.8 | 2.7 | More than 1000 ml throughput without plugging |
| Treated-1 hour | 4.65 | 7.0 | 0.1 | Filter plugged at 12 ml |

TABLE 6-continued

EFFECT OF SALINE HEAT TREATMENT AT 121° C. ON VISCOSITY AND FILTERABILITY OF VARIOUS HETEROPOLYSACCHARIDE SOLUTIONS IN 8.8% BRINE[a]

| | Filterability[b] | | |
|---|---|---|---|
| Vis.[b] | Flow Rate (ml/min)[c] | | |
| (cp) | @ 100 ml | @ 1000 ml | Remarks |
| | | | More than 1000 ml throughput without plugging |

[a] Saline heat treatment was done using 3,000 ppm heteropolysaccharide concentrates in 2.2% brine.
[b] Filterability and viscosity measurements were done on the 600 ppm heteropolysaccharide solutions in 8.8% brine.
[c] Flow rates are shown for the points at which 100 or 1000 ml of solution had passed through the filter.

TABLE 7

EFFECT OF SALINE HEAT TREATMENT 121° C. ON VISCOSITY AND FILTERABILITY OF VARIOUS HETEROPOLYSACCHARIDE SOLUTIONS IN 1.76% BRINE[a]

| | Filterability[b] | | |
|---|---|---|---|
| Vis.[b] | Flow Rate (ml/min)[c] | | |
| (cp) | @ 100 ml | @ 1000 ml | Remarks |
| Sample A | | | |
| Untreated | 5.60 | 4.0 | 2.4 | More than 1000 ml throughput without plugging |
| Treated-3 hours | 4.95 | 11.0 | 5.4 | More than 1000 ml throughput without plugging |
| Sample B | | | |
| Untreated | 5.10 | 8.7 | — | Filter plugged at 210 ml |
| Treated-3 hours | 4.30 | 16.8 | 3.5 | More than 1000 ml throughput without plugging |
| Sample C | | | |
| Untreated | 5.70 | — | — | Filter plugged at 54 ml |
| Treated-3 hours | 5.20 | 10.5 | 3.1 | More than 1000 ml throughput without plugging |
| Sample D | | | |
| Untreated | 6.05 | — | — | Filter plugged at 85 ml |
| Treated-3 hours | 5.10 | 11.0 | 3.2 | More than 1000 ml throughput without plugging |
| Sample E | | | |
| Untreated | 4.20 | 7.0 | 4.4 | More than 1000 ml throughput without plugging |
| Treated-3 hours | 3.00 | 20.0 | 15.0 | More than 1000 ml throughput without plugging |
| Sample F | | | |
| Untreated | 5.70 | — | — | Filter plugged at 20 ml |
| Treated-3 hours | 3.00 | 21.0 | 0.3 | More than 1000 ml throughput without plugging |
| Treated-1 hour | 4.20 | 9.0 | 0.2 | More than 1000 ml throughput without plugging |

[a] Saline heat treatment was done using 3,000 ppm heteropolysaccharide concentrates in 2.2% brine.
[b] Filterability and viscosity measurements were done on the 600 ppm heteropolysaccharide solutions in 1.76% brine.
[c] Flow rates are shown for the points at which 100 or 1000 ml of solutions had passed through the filter.

EXAMPLE VII

A 3000 ppm concentrate of heteropolysaccharide biopolymer containing 2.2% salts was prepared and treated as in Example II. The flask containing the concentrate was heat treated at 121° C. for 3 hours. The flask was cooled to approximately 80° C. and prefiltered through a 47 mm diameter Millipore AP-25 ® prefilter pad followed by a 47 mm diameter 1.2 Millipore ® filter with an AP-25 prefilter pad. This prefiltered 3000 ppm concentrate was used to prepare 600 ppm polymer solutions containing 1.76% and 8.8% salts without any further prefiltrations. Viscosities and injectivities were determined as in Example II. The results are tabulated below:

| Brine Concentration (%) | 1.76 | 8.8 |
|---|---|---|
| Viscosity (cp) | 5.0 | 5.5 |
| Flow Rate (ml/min) | | |
| @ 100 ml | 14.0 | 12.0 |
| @ 1000 ml | 7.5 | 5.8 |
| Total throughput (ml) | More than 1000 ml throughput without plugging | |

The above data indicate that the shear step on the 3000 ppm heteropolysaccharide concentrate used in Example II, as well as the prefiltrations on the diluted 600 ppm heteropolysaccharide solutions are not absolutely required to achieve solutions with appropriate viscosity and injectivity characteristics.

EXAMPLE VIII

Three sets of flasks of 3000 ppm heteropolysaccharide concentrate were prepared and heat treated as in Example II for one hour at 121° C. The flasks were then cooled to 80° C. To the first set of flasks was added 500 ppm of trichlorophenol. To the second was added 500 ppm of 2-pyridinethiol 1-oxide (sodium omadine). The third set was not treated with a biocide and was used as a control. The 3000 ppm concentrates containing the biocides as well as the control were filtered and diluted to 600 ppm heteropolysaccharide in 1.76 and 8.8% brine as in Example VI. Injectivity, viscosity and viability data were obtained immediately, after 3 days, and after 7 days of storage at room temperature. Results are shown in Table 8.

TABLE 8

EFFECT OF BIOCIDE ADDITION ON
HETEROPOLYSACCHARIDE SOLUTIONS

|  | No biocide added (Control) | Solution aged 3 days with: | | Solution aged 7 days with: | |
| --- | --- | --- | --- | --- | --- |
|  |  | Trichloro-phenol | Sodium Omadine | Trichloro-phenol | Sodium Omadine |
| 1.76% Brine | | | | | |
| Flow Rate (ml/min) | | | | | |
| @ 100 ml | 14.0 | 9.0 | 14.0 | 11.5 | 15.0 |
| @ 1000 ml | 7.5 | 3.0 | 10.0 | 6.0 | 9.5 |
| Total Throughput (ml) | More than 1000 ml throughput without plugging → | | | | |
| Viscosity (cp) | 5.0 | 5.1 | 5.0 | 5.15 | 4.9 |
| Viable Count (Organisms/ml) | <1 | <1 | <1 | <1 | <1 |
| 8.8% Brine | | | | | |
| Flow Rate (ml/min) | | | | | |
| @ 100 ml | 12.0 | 9.8 | 14.0 | 10.0 | 14.0 |
| @ 1000 ml | 5.8 | 1.0 | 7.0 | 3.0 | 8.0 |
| Total Throughput (ml) | More than 1000 ml throughput without plugging → | | | | |
| Viscosity (cp) | 5.5 | 5.5 | 5.5 | 5.5 | 5.4 |
| Viable Count (Organisms/ml) | <1 | <1 | <1 | <1 | <1 |

The data clearly demonstrate that biocides may be added to saline heat treated heteropolysaccharide solutions without viscosity impairment or substantial change in injectivity of the heteropolysaccharide solution. The viable count data demonstrate that at 100 ppm biocide concentration, the biocide appear to have been effective in preventing bacterial growth for at least 7 days.

EXAMPLE IX

Concentrates containing 3000, 6000, 9000, and 12,000 ppm of heteropolysaccharide were prepared as in Example II. The flasks containing the various concentrates were heat treated at 121° C. for 3 hours. The flasks were cooled to room temperature. The 6000, 9000, and 12,000 ppm heteropolysaccharide concentrates were then diluted to 3000 ppm concentration at 2.2 weight percent brine. All concentrates were then prefiltered as in Example VII. These prefiltered 3000 ppm concentrates were then used to prepare 600 ppm heteropolysaccharide solutions in 8.8 weight percent brine. Viscosities and injectivities were determined as in Example II. The results are tabulated below:

|  | Heteropolysaccharide Concentration During Saline Heat Treatment (ppm) | | | |
| --- | --- | --- | --- | --- |
|  | 3000 | 6000 | 9000 | 12,000 |
| Flow Rate (ml/min) | | | | |
| @ 100 ml | 11.5 | 11.0 | 11.0 | 10.0 |
| @ 1000 ml | 5.6 | 5.3 | 5.3 | 3.0 |
| Total Throughput (ml) | More than 1000 ml without plugging | | | |
| Viscosity (cp) | 5.8 | 5.85 | 5.95 | 5.6 |

The data clearly demonstrate that heteropolysaccharide concentrates of 3000–12,000 ppm may be saline heat treated without impairment of viscosity and still maintain superior injectivity.

EXAMPLE X

A 3000 ppm heteropolysaccharide concentrate was prepared, saline heat treated for one hour at 121° C., and prefiltered according to the procedure outlined in Example II.

A sample of the treated material was used to prepare a 600 ppm heteropolysaccharide solution in 8.8% brine according to Example III. The viscosity and injectivity were determined.

The remainder of the modified heteropolysaccharide concentrate was precipitated with methanol. The recovered modified heteropolysaccharide was dried, milled, and rehydrated to 3000 ppm in 2.2 weight percent brine with a magnetic stirrer. A sample of this rehydrated concentrate was used to prepare a 600 ppm modified heteropolysaccharide solution in 8.8 weight percent brine. The viscosity and injectivity were determined. A table of the results is shown below:

|  | Flow Rate (ml/min) | | Vis. | Remarks |
| --- | --- | --- | --- | --- |
|  | @ 100 ml | @ 1000 ml | (cp) | |
| No Saline Heat Treatment | — | — | 5.8 | Filter plugged at 35 ml |
| No Saline Heat Treatment, Methanol-Precipitated | — | — | 5.75 | Filter plugged at 42 ml |
| Saline Heat Treatment | 11.0 | 5.0 | 5.70 | More than 1000 ml throughput without plugging |
| Saline Heat Treatment, Methanol-Precipitated | 5.8 | 2.0 | 7.5 | More than 1000 ml throughput without plugging |

The above data indicate once again that the saline heat treated material (i.e., the modified heteropolysaccharide of the present invention) is superior to the non-heat treated material. They also clearly demonstrate that the saline heat treated material (i.e. the modified heteropolysaccharide) may be recovered by standard procedures and hydrated with retention of desirable injectivity and viscosity characteristics.

EXAMPLE XI

Example XI illustrates that the saline heat treatment can be applied directly to Xanthomonas fermentation broth, and moreover, that such saline heat treated broth can be dried by simple means and subsequently reconstituted to produce solutions containing the modified heteropolysaccharides having the desired properties. To 500 ml samples of Xanthomonas campestris fermentation broth, containing 20,000 ppm of heteropolysaccharide was added 10 grams of NaCl and 1.0 gram of CaCl$_2$. The salts were dissolved by mixing in a Waring Blendor ® at low speed for two minutes and at full power for three minutes. The salt-supplemented fermentation broth was placed in a flask which was then capped tightly with aluminum foil and Saran-Wrap ® and heated in an autoclave at 121° C. for one hour. After saline heat treatment the flask was cooled to room temperature. The treated broth was diluted to a 4000 ppm heteropolysaccharide biopolymer concentration with a solution containing 2% NaCl and 0.2% CaCl$_2$. The treated and diluted broth was vacuum filtered through the following series of 47 mm diameter Millipore ® filters: AP-25; 1.2 micron; 0.8 micron; 0.65 micron; and 0.45 micron. Two 200 gram samples of the final filtrate were used to prepare solutions containing 800 ppm of polymer in 1.76% and 8.8% brine. Two additional 200 gram samples of the final filtrate were placed in beakers which were then placed in a heated vacuum oven for 18 hours. After cooling, the modified heteropolysaccharide in the beakers was used to prepare solutions containing 800 ppm of heteropolysaccharide in 1.76% and 8.8% brine. The solutions were sheared in a Waring Blendor ® at 19,000 rpm for 30 seconds and 2 minutes, respectively, and filtered through a 47 mm diameter, 0.8 micron Millipore ® filter. The data for the viscosity and injectivity tests for the saline heat treated broth and the saline heat treated, dried, and reconstituted broth as compared with data for fermentation broth that had not been subjected to any saline heat treatment are shown in Table 9.

TABLE 9

| | Fermentation Broth | | |
|---|---|---|---|
| | No Saline Heat Treatment | Saline Heat Treated | Saline Heat Treated Dried & Reconstituted |
| 1.76% Brine | | | |
| Flow Rate (ml/min) | | | |
| @ 100 ml | 1.8 | 7.0 | 6.4 |
| @ 1000 ml | 0 | 3.5 | 2.5 |
| Viscosity (cp) | 6.6 | 8.7 | 7.7 |
| Total Throughput (ml) | Filter plugged at 253 ml | More than 1000 ml throughput without plugging | |
| 8.8% Brine | | | |
| Flow Rate (ml/min) | | | |
| @ 100 ml | 2.3 | 6.5 | 8.5 |
| @ 1000 ml | 0 | 3.3 | 4.5 |
| Viscosity (cp) | 7.0 | 9.2 | 7.6 |
| Total Throughput (ml) | Filter plugged at 336 ml | More than 1000 ml throughput without plugging | |

The above data indicate that crude Xanthomonas fermentation broth can be saline heat treated directly by the method of this invention to produce a solution with appropriate viscosity and injectivity characteristics. Moreover, such saline heat treated fermentation broth can be treated by simple means, without resort to solvent precipitation steps, and subsequently reconstituted to produce a solution with appropriate viscosity and injectivity characteristics.

EXAMPLE XII

Example XII shows the physical difference between the saline heat treated heteropolysaccharide solutions of this invention and solutions of heteropolysaccharide which have not been subjected to the saline heat treatment. This Example shows that the saline heat treatment results in a marked decrease in the average particle size of the heteropolysaccharide.

To eliminate the effect of bacterial cells and other debris in the untreated heteropolysaccharide solution, it was first subjected to ultracentrifugation. In this process, aqueous solutions of the heteropolysaccharide at a concentration of 2000 ppm were placed in a Beckman L2-65B centrifuge with a Ti-60 rotor and centrifuged at 45,000 rpm for 3 hours at approximately 15° C. After this ultracentrifugation, the clear heteropolysaccharide solution was decanted from the bacterial cells which had collected at the bottom of the centrifuge vessel and was inspected microscopically. Observation of the centrifuged heteropolysaccharide solution under 430X magnification indicated that essentially all bacterial cells and other debris had been removed from the solution. In addition, the cellular debris from the centrifuge vessel was resuspended at a concentration of 2000 ppm, and a cell count was obtained with a 430X microscope. The cell count of the resuspended material was substantially the same as in the heteropolysaccharide solution prior to centrifugation, again indicating that essentially all bacterial cells had been removed from the heteropolysaccharide solution by centrifugation.

To determine the relative particle size of heteropolysaccharide which had been treated as shown in Example II for one hour at 121° C. and heteropolysaccharide which had been subjected to ultracentrifugation but otherwise untreated, a series of tests were conducted on aqueous solutions of treated and untreated heteropolysaccharide each containing 2 wt. % NaCl and 0.2 wt. % CaCl$_2$. These solutions, as well as distilled water, were passed through Nuclepore ® filters of varying pore sizes at varying flow rates at about 22° C. The pressure drop across the filters at each flow rate was determined using a manometer, and these values were normalized by determining the slope of the pressure drop-flow rate curve for each heteropolysaccharide solution with a given filter size and dividing this slope by the corresponding slope of the curve for water. This ratio is the "Effective Viscosity" for the solutions and normalizes the measured pressure drop values to remove differences which are due to variations in filter pore geometry. A sharply higher value for Effective Viscosity for a heteropolysaccharide solution compared to the value obtained for a second solution in passing through the same sized filter is indicative that the first solution contains heteropolysaccharide having a larger average particle size than the heteropolysaccharide in the second solution.

In conducting these tests to determine the Effective Viscosity for polymer solutions, a fluid-(water, aqueous solution of treated heteropolysaccharide containing 2 wt. % NaCl and 0.2 wt. % CaCl$_2$ or aqueous solution of untreated heteropolysaccharide containing 2 wt. % NaCl and 0.2 wt. % CaCl$_2$) was withdrawn from a storage reservoir by means of peristaltic pump and passed through a Nuclepore ® filter at a specific flow rate at about 22° C. The pressure drop across the filter was maintained within the range of 0.2 to 100 centimeters of water and was measured as soon as possible at a given flow rate to avoid pressure drops due to plugging of the filter. Subsequently, the flow rate was increased to higher levels and the pressure drop at each flow rate was determined. Finally, the system was returned to the original flow rate to assure that the original pressure drop could be duplicated. When the original pressure drop could not be duplicated with a particular heteropolysaccharide solution and with a given filter pore size, this was an indication that this heteropolysaccharide was plugging the filter.

Table 10 shows the Effective Viscosities for treated and untreated heteropolysaccharide samples when passed across Nuclepore ® filters ranging in size from 8 microns to 0.2 microns.

The data in this Table were obtained by testing aqueous solutions of Xanthomonas heteropolysaccharide which had been subjected to the saline heat treatment illustrated in Example II and aqueous solutions of Xanthomonas heteropolysaccharide which had been subjected to ultracentrifugation but otherwise untreated. The solutions contained heteropolysaccharide at a concentration of 600 ppm and 2 wt. % NaCl and 0.2 wt. % $CaCl_2$.

TABLE 10

| Heteropoly-saccharide | EFFECTIVE VISCOSITY | | | | | | |
|---|---|---|---|---|---|---|---|
| | Nuclepore ® Filter Size (microns) | | | | | | |
| | 8.0 | 5.0 | 3.0 | 1.0 | 0.8 | 0.4 | 0.2 |
| Treated | 3.0 | 2.9 | 2.8 | 3.0 | 2.9 | 3.2 | 30.0 |
| Untreated | 3.3 | 3.2 | 3.6 | 7.7 | 10.9 | * | * |

*filter plugged

As can be seen from the data presented in Table 9 the saline heat treated heteropolysaccharide shows no appreciable rise in Effective Viscosity until the Nuclepore ® filter size is reduced below 0.4 microns. However, the untreated heteropolysaccharide solution shows some rise in Effective Viscosity at 3 microns and an Effective Viscosity of almost 8 at a pore size of 1 micron. At a filter pore size of 0.8, the native unmodified heteropolysaccharide has an effective viscosity of 10.9 which is nearly four times the Effective Viscosity of the modified heteropolysaccharide of the present invention. At pore sizes of 0.4 microns and less, the Effective Viscosity of the untreated material (the native unmodified heteropolysaccharide) is too high to measure. These data demonstrate that the saline heat-treating process materially reduces the average particle size of the heteropolysaccharide.

It should also be noted that the heteropolysaccharide of this invention retains its ability to increase the viscosity of its aqueous solutions. Thus the heteropolysaccharide in addition to having an Effective Viscosity at about 22° C. in aqueous solution containing 2 wt. % NaCl and 0.2 wt. % $CaCl_2$ at a concentration of 600 ppm of less than 5 when passed through a Nuclepore ® filter having a pore size of 1 micron, must have a viscosity in a 600 ppm concentration aqueous solution containing 2 wt. % NaCl and 0.2 wt. % $CaCl_2$, of at least 4.0 centipoises when measured in a Brookfield viscosimeter with a UL adapter at 60 rpm and 25° C.

ADDITIONAL TESTS FOR CHARACTERIZING THE MODIFIED HETEROPOLYSACCHARIDES

A number of tests were performed to establish that the modified heteropolysaccharide of the present invention differs from native, unmodified heteropolysaccharide, both chamically and physically.

In these tests (as more fully described in the following examples) and native, unmodified heteropolysaccharide used was obtained from Kelco Company (Ketrol Lot No. 16573). This material contains cells and other undesired debris; CHN analysis shows 38% C, 55% H, and 1.2% N. Prior to testing, the native, unmodified heteropolysaccharide was purified by a modification of the procedure described in Jeanes, A., Pittsley, J. E. and Senti, F. R., J. Appl. Polym. Sci. 5, 519–526 (1961). The heteropolysaccharide was dissolved to 0.3 g/l in water and stirred overnight. NaCl (0.34 M) and EDTA (0.0025 M) were then added and the solution was mixed for 10 minutes at lowest speed with an Oster Model 847-01A blender. After adjusting the solution to pH 7, ethanol (300 m/l of $H_2O$) was added. The solution was centrifuged at 45,000 rpm for 90 minutes to remove cells, debris, and undispersed heteropolysaccharide. The supernatant $S_1$ was decanted and additional ethanol was added to $S_1$ (440 ml/l of $H_2O$) to precipitate the heteropolysaccharide as a soft gel which was easily separated by centrifugation at 12,000 rpm for 30 minutes. The precipitate $P_2$ thus obtained was redissolved in water; EDTA and NaCl were then added (0.0025 and 0.43 M, respectively).

The heteropolysaccharide was reprecipitated with ethanol (1 ml/ml of $H_2O$) and then again centrifuged at 12,000 rpm for 30 minutes to isolate precipitate $P_3$. This material was redissolved in water and dialyzed exhaustively against redistilled deionized water at 5° C. The "yield" was typically 60–70%. This material was used immediately except where otherwise indicated. CHN analysis of the native, unmodified heteropolysaccharide revealed 39% C, 5.6% H, and 0.03% N (Kjeldahl).

The modified heteropolysaccharide used in the tests described in the following examples was prepared in the following manner.

The modified heteropolysaccharide was prepared from the native, unmodified heteropolysaccharide, Keltrol ® (Lot No. 16573 from Kelco Company). 1 g of Keltrol native, unmodified heteropolysaccharide was dissolved in 450 ml of $H_2O$ and stirred overnight at 5° C. Thereafter, 10 g of NaCl in 50 ml $H_2O$ was added to the heteropolysaccharide solution. This solution was mixed for 10 minutes in an Oster blender at lowest speed. The pH was monitored and adjusted as necessary with 0.1 N HCl or 0.1 N NaOH as required to maintain the pH at 7.0±0.2. The solution was centrifuged for 1.5 hours at 45,000 rpm using a Type 60 Ti rotor in a Beckman L2-65 ultracentrifuge at 15° C. (143,000×g average force). The centrifuge tubes were decanted and the combined supernatants were saved as $S_1$. The volume of $S_1$ was measured, 0.2% by weight $CaCl_2$ was added, and the pH was again checked and adjusted to 7.0±0.2 if required. The solutions containing the salts and heteropolysaccharide were heated in a Saran Wrap ® sealed 1-liter filter-flask for 1 hour at 121° C. (at 15 psig) in an autoclave. The hot liquid was filtered in five (5) sequential filtrations through a series of 25 mm diameter Millipore ® filters having the following designated pore size.

1. 5 μm + prefilter (Millipore AP-25)
2. 1.2 μm + prefilter (Millipore AP-25)
3. 0.8 μm + prefilter (Millipore AP-25)
4. 0.65 μm + prefilter (Millipore AP-25)
5. 0.45 μm + prefilter (Millipore AP-25)

The pH was checked again and adjusted to 7.0±0.2 if necessary. The resulting test solution contained approximately 1200–1800 ppm modified heteropolysaccharide containing 2.2 wt. % salt. This test solution was further purified by repeatedly precipitating with ethanol and redissolving in $H_2O$ as described above with respect to the native, unmodified heteropolysaccharide, followed by redissolution in water and exhaustive dialysis against deionized water at 5° C. The resulting purified modified heteropolysaccharide solution was used immediately except where otherwise indicated.

EXAMPLE XIII

Electron micrographs of native, unmodified heteropolysaccharide and the modified heteropolysaccharide prepared as described in Example XII were obtained by spraying a dilute heteropolysaccharide solution (approximately 6 ppm) in 0.01 M ammonium acetate buffer onto a "reactive" carbon substrate. This reactive substrate was prepared by evaporation of carbon with $10^{-4}$–$10^{-5}$ kPa of air remaining; this is the point at which the carbon began to spark instead of evaporating smoothly. The resulting carbon films have reactive sites for the deposition of the heteropolysaccharide. A microdrop of a 6 ppm heteropolysaccharide solution was placed in the center of a standard electron microscope grid covered with the carbon film, allowed to dry in air, then shadowed with uranium at an angle corresponding to $\tan^{-1}(\frac{1}{4})$. The shadowed preparations were examined using a Philips EM 300 electron microscope having a resolution greater than 0.3 nm. Magnification calibration of the micrographs was obtained from measurement of spacings of the $Ti_4O_7$ lattice.

Electron micrographs of native, unmodified heteropolysaccharide show the molecules to be 2 to 10 μm long, generally smooth, unbranched, and with a thickness of 4 nm in their thickest regions. The modified heteropolysaccharide molecules, in contrast, were 1–2 μm long, 4 nm thick, and occasionally exhibited short unravelled regions.

EXAMPLE XIV

The sedimentation rate of the native, unmodified heteropolysaccharide and of modified heteropolysaccharide was measured by zone sedimentation. In order for the sedimentation to proceed at sufficiently low concentration, both the native and the modified heteropolysaccharide were lightly labeled with a covalently linked fluorescent group.

Three typical heteropolysaccharide test solutions were prepared as follows. The first, designated sample A, was native, unmodified Keltrol ® purified of cells and other debris by a brief centrifugation. An aliquot of this purified, native heteropolysaccharide, dissolved in water containing by weight 2% NaCl and 0.2% $CaCl_2$, was heat-treated for 1 hour at 121° C. to obtain sample B, modified but unfiltered heteropolysaccharide. Finally, an aliquot of B was filtered through an 0.45 μm Millipore ® filter and designated as sample C. Samples A, B, and C were each covalently labeled with a fluorescent amine by the isocyanide coupling reaction. The three fluorescent samples, designated A*, B*, and C*, were then diluted to a final concentration of 6 ppm whereupon 0.5 ml of sample was layered onto the top of a 4–8% NaCl gradient in 15 ml ultracentrifuge tubes. The samples were sedimented at 20° C. for 3.5 hours in a Beckman SW-40 rotor at a speed of 40,000 rpm. The position of the band after sedimentation was established by recording fluorescence intensity versus distance down the centrifuge tube; results are given in Table 11 below.

TABLE 11

POSITION OF HETEROPOLYSACCHARIDE BAND IN CENTRIFUGE TUBE AFTER SEDIMENTATION

| Distance from Meniscus cm | Relative Fluorescence Intensity[a] | | | Sedimentation Constant, S[b] |
|---|---|---|---|---|
| | A* | B* | C* | |
| 0 | 0 | 0 | 0 | |
| .407 | 0 | .2 | .2 | |
| .814 | .2 | .8 | .9 | |
| 1.22 | 1.1 | 2.9 | 3.2 | |
| 1.63 | 3.0 | 8.6 | 8.0 | |
| 2.04 | 6.5 | 16.0 | 15.5 | 9.8 |
| 2.44 | 10.1 | 17.6 | 17.9 | |
| 2.85 | 11.9 | 14.8 | 15.6 | |
| 3.26 | 11.5 | 11.1 | 11.4 | |
| 3.66 | 9.9 | 7.5 | 7.5 | |
| 4.07 | 8.3 | 5.1 | 5.1 | 19.1 |
| 4.48 | 6.8 | 3.4 | 3.4 | |
| 4.88 | 5.5 | 2.6 | 2.3 | |
| 5.29 | 4.5 | 1.9 | 1.7 | |
| 5.70 | 3.7 | 1.3 | 1.2 | |
| 6.11 | 3.0 | 1.1 | 0.9 | 26.4 |
| 6.51 | 2.6 | 0.9 | 0.7 | |
| 6.92 | 2.2 | 0.7 | 0.6 | |
| 7.33 | 1.8 | 0.7 | 0.4 | |
| 7.73 | 1.7 | 0.6 | 0.4 | |
| 8.14 | 1.7 | 0.6 | 0.4 | 32.4 |
| 8.55 | 1.7 | 0.6 | 0.3 | |
| 8.95 | 3.7 | 1.3 | 1.3 | |
| Bottom of Tube | — | — | | |

[a] The values are normalized so that the area under each curve is the same. A* is native heteropolysaccharide; B* is modified but unfiltered heteropolysaccharide; C* is modified and filtered heteropolysaccharide.
[b] Evaluated from the relation $S = \Delta r/(w^2 \Delta t\, \bar{r})$ where $\Delta r$ is the distance the band moves during sedimentation, w is the rotational speed of the rotor, $\Delta t$ is the sedimentation time, and $\bar{r}$ is the mean distance of the band from the center of the rotor. The units of S are $10^{-13}$ sec.

The last column in Table 11 lists the sedimentation coefficient at several points down the tube, for the particular conditions used in this experiment.

The results shown in Table 11 lead to several conclusions about the difference between native and modified heteropolysaccharide:

1. The breadth of each band, compared to the breadth of the starting zone, shows that the heteropolysaccharides are polydisperse, with sedimentation coefficient varying over a broad range. This is especially notable for the unmodified heteropolysaccharide, sample A*.
2. The average sedimentation coefficient of the samples is as follows: A*=19.5 S; B*=15.4 S; C*=15.1 S. These values are calculated by averaging $\Delta r/r$ over each band, weighting each point according to the relative fluorescence intensity at that point in the tube. The results demonstrate that heat-treatment diminishes the average sedimentation coefficient of the heteropolysaccharide.
3. The distribution of sedimentation rates is even more markedly affected by heat treatment than are the average sedimentation rates. In particular, native heteropolysaccharide (Sample A*) has substantially more material with very large sedimentation rate (high molecular weight) than do the modified heteropolysaccharide Samples B* and C*. In the present case 18% of Sample A* has sedimentation coefficient equal to 26 S or greater, whereas only 6–7% of Samples B* and C* possess such a large sedimentation coefficient.
4. The distribution of sedimentation coefficient is greatly affected by heating for 1 hour at 121° C. (difference between A* and B*) but only slightly affected by filtration subsequent to heating (difference between B* and C*).

EXAMPLE XV

Membrane partition chromatograms were carried out with solutions of native, unmodified heteropolysaccharide and modified heteropolysaccharide of the present invention at a concentration of 500 ppm in aqueous solvent containing 2% NaCl, 0.2% CaCl$_2$, pH 7. An eight channel Technicon ® peristatic pump was used to drive the heteropolysaccharide solution at a rate of 1 ml/hr independently to eight Nuclepore ® filters. Each filter was 25 mm in diameter; pore diameters were 0.05 to 5 $\mu$m. About 1.5 ml of the fluid transmitted by each filter was collected and analyzed for carbohydrate content by the phenol-H$_2$SO$_4$ method (M. Dubois et al., *Analyt. Chem.* 28, 350–356 (1956). The fraction of carbohydrate transmitted was then evaluated. Typical results are given in Table 12 below.

TABLE 12
MEMBRANE PARTITION CHROMATOGRAM

| Pore Size, $\mu$m | Fraction Carbohydrate Transmitted | |
|---|---|---|
| | Unmodified | Modified |
| .05 | | .14 |
| .08 | | .14 |
| .1 | .03 | .15 |
| .2 | .04 | .19 |
| .4 | .15 | .62 |
| .6 | .58 | .98 |
| .8 | .69 | 1.00 |
| 1.0 | .98 | 1.00 |
| 3 | 1.00 | |
| 5 | 1.00 | |

A pore size of about 0.6 $\mu$m keeps about 40% by weight of the native, unmodified molecules back, whereas a pore size of 0.4 m is needed to achieve the same result for the modified heteropolysaccharide traverses even 0.05 and 0.8 $\mu$m pores whereas only 3% of the native, unmodified heteropolysaccharide can pass a 0.1 $\mu$m pore.

EXAMPLE XVI

A. Precipitation of heteropolysaccharide by the quaternary ammonium salt cetyltrimethylammonium bromide in the presence of various amounts of NaCl was carried out according to the procedure of J. E. Scott, *Methods of Carbohydrate Chem.* 5, 38–44 (1965). This experiment shows that native, unmodified heteropolysaccharide is half-precipitated at 0.27 M NaCl whereas treated heteropolysaccharide is half-precipitated at 0.23 M NaCl. The direction of the change means that native, unmodified heteropolysaccharide binds the precipitating agent, cetyltrimethylammonium bromide, more strongly than modified heteropolysaccharide, because of higher charge density on the native biopolymer.

B. Precipitation of the heteropolysaccharides with water by ethanol was examined in the presence of 2% NaCl, 0.2% CaCl$_2$, 0.01 M Tris buffer, pH 7. One-half of the native, unmodified heteropolysaccharide is precipitated at an ethanol volume fraction of 0.394, whereas one-half of the modified heteropolysaccharide of the present invention is precipitated at ethanol volume fraction 0.359.

C. Precipitation of the heteropolysaccharides by various amounts of Fe$^{+3}$ ion was studied in the presence of 1% CaCl$_2$, 0.01 M ammonium acetate buffer, pH 7. It was found that, for heteropolysaccharide concentration equal to 300 ppm, one-half of the native, unmodified heteropolysaccharide is precipitated at 0.62×10$^{-4}$ M FeCl$_3$, whereas precipitation of one-half of the modified heteropolysaccharide requires 1.05×10$^{-4}$ M FeCl$_3$. This implies that the native, untreated heteropolysaccharide has more binding sites for Fe$^{+3}$. Otherwise stated, the modified heteropolysaccharide of the invention has fewer binding sites for Fe$^{+3}$ than the native, unmodified heteropolysaccharide.

EXAMPLE XVII

Determination of acetyl content of native, unmodified heteropolysaccharide and the modified heteropolysaccharide of the present invention was carried out by the method of Sutherland and Wilkinson, *Biochem J.* 110, 749–754 (1968). Three preparations of Xanthomonas-produced heteropolysaccharide were purified and lyophilized as described by Holzwarth, *Biochemistry* 15, 4333–4339 (1976). Three further batches of the modified and purified Xanthomonas-produced heteropolysaccharide of the present invention which had been repurified and lyophilized as described above were obtained for this test. The determination of the acetyl content then proceeded as follows. Three mg of dry heteropolysaccharide were dissolved in 1 ml water. To this was added 2 ml of a solution containing 1 part 2 M hydroxylaminehydrochloride and 1 part 3.5 M NaOH. After 1 minute 1 ml of 3.5 M HCl was added, followed by 1 ml FeCl$_3$ solution (0.37 M in 0.1 N HCl). The optical density was then read at 540 nm. Ethyl acetate solutions (1×10$^{-3}$ to 6×10$^{-3}$ M) were used in place of the polymer to standardize the relationship between optical density and acetyl content. Typical triplicate determinations for native, unmodified heteropolysaccharide and modified heteropolysaccharide of the present invention gave the following data.

| Sample | Heteropoly-saccharide, mg | OD$_{540}$ | OD$_{540}$/mg | g (Polymer) per mole (Acetyl) |
|---|---|---|---|---|
| Native | 3.1 | 0.617 | 0.199 | 774 |
| Native | 3.2 | 0.649 | 0.203 | 759 |
| Native | 3.1 | 0.622 | 0.201 | 767 |
| Native Mean | | | | 767 |
| Modified | 2.8 | 0.514 | 0.184 | 837 |
| Modified | 2.7 | 0.464 | 0.172 | 896 |
| Modified | 3.5 | 0.654 | 0.187 | 824 |
| Modified Mean | | | | 852 |

The percentage change in acetyl content is 100×(852−767)/767 or 11% in this case.

EXAMPLE XVIII

In this experiment the pyruvate content of native, unmodified heteropolysaccharide and modified heteropolysaccharide of the present invention was determined. The method used was the lactate dehydrogenase-NADH method described by Duckworth and Yaphe, *Chemistry and Industry* (1970) p. 747. Purified, lyophilized, native, unmodified heteropolysaccharide and purified, lyophilized, modified heteropolysaccharide of the present invention were tested. The final step in the test is measurement of the amount of NADH converted to NAD by the pyruvic acid released from the heteropolysaccharide. This is monitored by the change in optical density at 340 nm. Typical results for a triplicate determination on one native, unmodified heteropolysaccharide and one modified heteropolysaccharide sample were as follows:

| Sample | Polymer, mg | OD$_{340}$ | OD/mg |
|---|---|---|---|
| Native | 5.3 | .474 | 1.34 |
| Native | 5.1 | .435 | 1.28 |
| Native | 5.0 | .494 | 1.48 |
| Native Mean | | | 1.37 |
| Treated | 4.7 | .328 | 1.05 |
| Treated | 4.5 | .313 | 1.04 |
| Treated | 5.3 | .385 | 1.09 |
| Treated Mean | | | 1.06 |

The percentage decrease in pyruvate content upon treatment, $100 \times (1.37-1.06)/1.37$, equals 23% in this instance.

GENERAL

As seen from the above description of the invention, the modified heteropolysaccharides of the present invention possess a unique combination of properties rendering them useful in a plurality of applications. In addition, the saline heat treatment process not only provides the new modified heteropolysaccharides but also unexpectedly facilitates the separation of the heteropolysaccharide from cellular debris and other fermentation materials, whether the separation is by centrifugation or by filtration. While not wishing to be bound by any theory, it is believed that the saline heat treatment selectively agglomerates the cellular debris and other fermentation material which renders these materials more amenable for separation from the heteropolysaccharide.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention.

What is claimed is:

1. A process for recovering oil from a subterranean formation penetrated by at least one injection well and at least one production well by injecting an amount effective to provide mobility control of an aqueous solution containing a heteropolysaccharide produced by the action of bacteria of the genus Xanthomonas into said injection well and into said subterranean formation to displace oil from the formation and producing oil from said subterranean formation by means of said production well, wherein said heteropolysaccharide has been prepared by a process comprising the steps of:
   (a) preparing an aqueous solution which contains
      (i) from about 200 to about 30,000 parts per million by weight, of said heteropolysaccharide, and
      (ii) at least about 0.5 weight percent of at least one inorganic salt to obtain a saline heteropolysaccharide solution;
   (b) heating said saline heteropolysaccharide solution to a temperature of at least about 100° C.;
   (c) maintaining said saline heteropolysaccharide solution at a temperature of at least about 100° C. for a period of time sufficient to increase the injectivity and filterability characteristics of the heteropolysaccharide but for an insufficient time to impair the viscosity imparting properties of the saline-heat treated heteropolysaccharide; and
   (d) removing or separating proteinaceous materials and/or residual whole bacterial cells or other cell debris from the saline and heat-treated heteropolysaccharide product to thereby obtain a modified heteropolysaccharide such that the modified heteropolysaccharide is capable of imparting a viscosity of at least 4.0 centipoises to an aqueous test solution containing 2 wt.% NaCl and 0.2 wt.% CaCl$_2$ when said modified heteropolysaccharide is added to said solution at a concentration of approximately 600 ppm, by weight, as measured on a Brookfield viscosimeter with a UL adapter at 60 rpm at 25° C. and said modified heteropolysaccharide is further capable of imparting a filterability such that more than 1000 ml of a different aqueous test solution containing 8.8 wt.% salt comprised of NaCl and CaCl$_2$ on a 10:1 wt. ratio and approximately 600 ppm concentration, by weight, of said modified heteropolysaccharide will pass without plugging through a Millipore ® filter having a diameter of 13 mm and a pore size of about 5 microns at a constant pressure drop of about 1.55 psig.

2. The process of claim 1 wherein said modified heteropolysaccharide is further characterized as capable of imparting an Effective Viscosity of less than about 5 to an aqueous test solution containing 2 wt.% NaCl and 0.2 wt.% CaCl$_2$ when said heteropolysaccharide in a filtered form is added to said aqueous test solution at a concentration of approximately 600 ppm when passed through a Nuclepore ® filter having a pore size of approximately 1 micron, said Effective Viscosity being defined as the normalized flow rate of the modified heteropolysaccharide divided by the normalized flow rate of distilled water when passed through said Nuclepore ® filter.

3. The process of claim 1 wherein said aqueous solution containing the modified heteropolysaccharide additionally contains an effective amount of a biocide.

4. The process of claim 3 wherein said biocide is a member selected from the group consisting of sodium trichlorophenate; 2,2-dibromo-3-nitrilpropionamide; 1-(3-chlorallyl)-3,5,7-triaza-1-azonia adamantane chloride; sodium O-phenylphenate; mixtures of sodium pentachlorophenate and sodium salts of other chlorophenols; sodium 2-pyridinethiol 1-oxide; zinc 2-pyridinethiol 1-oxide; mixtures of sodium trichlorophenate and methanol; formaldehyde and formalin solutions.

5. The process of claim 1 wherein said modified heteropolysaccharide is further characterized as having an average sedimentation coefficient of less than about $15.5 \times 10^{-13}$ sec.

6. The process of claim 1 wherein said heteropolysaccharide is produced by *Xanthomonas campestris*.

* * * * *